United States Patent [19]
Zheng et al.

[11] Patent Number: 5,629,433
[45] Date of Patent: May 13, 1997

[54] SELECTIVE PROCESS FOR THE DEACYLATION AND DEACETYLATION OF TAXOL AND TAXANES

[75] Inventors: Qun Y. Zheng, Superior; Lynn G. Darbie; Christopher K. Murray, both of Boulder, all of Colo.

[73] Assignee: Hauser, Inc., Boulder, Colo.

[21] Appl. No.: 276,254

[22] Filed: Jul. 18, 1994

[51] Int. Cl.$^6$ .................................................. C07D 305/14
[52] U.S. Cl. ........................................................ 549/510
[58] Field of Search ............................................ 549/510

[56] References Cited

U.S. PATENT DOCUMENTS

| | | | |
|---|---|---|---|
| 4,857,653 | 8/1989 | Colin et al. | 549/511 |
| 5,200,534 | 4/1993 | Rao | 549/510 |
| 5,256,801 | 10/1993 | Carver et al. | 549/510 |
| 5,274,137 | 12/1993 | Nicolaou et al. | 549/510 |

OTHER PUBLICATIONS

"Promotion of Microtubule Assembly in vitro by Taxol", Nature vol. 277:665–667 (1979) by S. Horwitz et al.

"Modified Taxols. 5. Reaction of Taxol with Electrophilic Reagents and Preparation of a Rearranged Taxol Derivative with Tubulin Assembly Activity", J. Org. Chem 56:5114–5119 (1991) by Kingston et al.

"The Chemistry of Taxanes: Reaction of Taxol and Baccatin Derivatives with Lewis Acids in Aprotic and Protic Media" Tetrahedron vol. 49, No. 14, pp. 2805–2828 (1993) by Chen et al.

Primary Examiner—Johann Richter
Assistant Examiner—John Peabody
Attorney, Agent, or Firm—Steven C. Petersen; Chrisman, Bynum & Johnson, P.C.

[57] ABSTRACT

The present invention relates to a highly selective method for the deacetylation and deacylation of taxol and taxanes compounds. Specifically, the present invention relates to a one step process wherein acyl groups located at the carbon 2', 10, and 7 positions of taxol and other taxane compounds may be selectively removed.

28 Claims, 3 Drawing Sheets

Taxol (IV)

Peroxide
Bases, solvent, r.t.

10-DAT (V)

SELECTIVE PROCESS FOR THE DEACYLATION AND DEACETYLATION OF TAXOL AND TAXANES

BACKGROUND OF THE INVENTION

1. Field of the Invention

The present invention relates to a highly selective method for the deacetylation and deacylation of taxol and taxanes compounds. Specifically, the present invention relates to a one step process wherein acyl groups located at the carbon 2', 10, and 7 positions of taxol and other taxane compounds may be selectively removed.

2. Description of the State of Art

Between the years 1958 and 1980, extracts of over 35,000 plant species were tested for anticancer activity as part of an NCI-sponsored program. Chemists Monroe E. Wall and M. C. Wani first isolated a crude extract concentrate from yew tree (*Taxus brevifolia*) bark and wood samples in 1963. Initial screening showed the extract to be a potential anticancer agent, being very active against an unusually wide range of rodent cancers. Isolation of the active agent in the crude extract took several years due to the very low concentrations of the agent present in the plants. The active agent was identified, the structure determined and the compound was named taxol, in 1971.

Cancer Institute (NCI) began a concerted effort to obtain taxol for clinical trials. In ongoing clinical trials, taxol has shown promising results in fighting advanced cases of ovarian, breast, and other cancers.

In spite of taxols excellent activity, its development as a clinical agent has been impeded both by the difficulty of isolation from the bark of the yew and its poor water-solubility. One approach to overcome the water-solubility drawback while possibly increasing potency is to develop various analogues of taxol. Taxotere is a new semisynthetic taxol analogue prepared at the Institut de Chimie des Substances Naturelie of the Centre National de la Recherche Scientifique (Gif sir Yvette, France). Taxotere was obtained through partial synthesis using a precursor 10-deacetylbaccatin III.

In a technical paper by Kingston et al., entitled "Modified Taxols. 5. Reaction of Taxol with Electrophilic Reagents and Preparation of a Rearranged Taxol Derivative with Tubulin Assembly Activity", *J. Org. Chem.* 56: 5114–5119 (1991) it was reported that taxol when treated under the mildest conditions of zinc bromide in methanol at ambient temperatures produces 10-deacetyltaxol (10-DAT) along with 10-deacetyl-7-epitaxol (7-epi-10-DAT). Selective deacetylation procedures were also reported by Chen et al, in "The Chemistry of Taxanes: Reaction of Taxol and Baccatin Derivatives With Lewis Acids in Aprotic and Protic Media," *Tetrahedron* 49(14): 2805–2828 (1993). Chen et al. reported

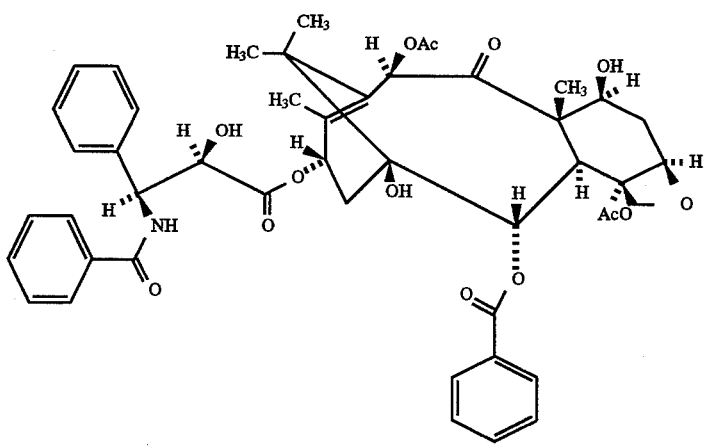

Despite taxol's excellent activity in model tumor systems, clinical trails were delayed owing to short supplies of the drug and formulation problems related to the drug's low water-solubility. However, great interest in the drug was rekindled when it was discovered in 1979 by Susan B. Horwitz and co-workers that a unique mechanism for taxol's antitumor activity involved cell microtubules. See, *Nature* 277: 665–667 (1979). Microtubules play a key role in mitosis, maintenance of cell shape, cell motility, and intracellular transport. They are self-assembling and self-disassembling structures that are in dynamic equilibrium with tubulin dimers, the protein subunits of which they are composed. A substance that interferes with microtubules can disrupt cell growth and function.

The 1979 study by S. Horwitz et al., reported that the binding of taxol to tubulin acts to stabilize cell microtubules and to prevent their depolymerization. Thus, taxol increases the time required for cell division which in turn inhibits tumor activity. Discovery of this unique mechanism, by which taxol disrupts the proliferation of cancerous cells, intensified research interest in the drug, and the National performing selective deacetylation using Lewis acids. All zinc halides used gave results analogous to the ones observed with zinc bromide. The same was hue for many salts tried, such as Ce (III) and Mg (II). Other Lewis acids (notably CsF and LiI) were found to cleave the side chain of taxol.

While it is possible to extract 10-deacetylbaccatin III (10-DAB) from the needles of the European Yew, *Taxus baccata*, it would be desirable to have a process that would convert other taxane compounds into 10-deacetylbaccatin III. While both Kingston et al. and Chen et al. report methods for the deacetylation of taxol resulting in compounds having greater water-solubility and new functional groups both methods suffer from the inability to entirely suppress the epimerization reaction at the C-7 position, thus resulting in low yields of 10-deacetyltaxol. A further disadvantage of the Lewis acids used by Chen et al. is that cleavage of the side chain readily occurs.

There is still a need, therefore, for a method for the selective deacylation including deacetylation of taxol and other taxanes so that various analogues of taxol having improved water-solubility and potency can be developed.

SUMMARY OF THE INVENTION

Accordingly, it is an object of this invention to provide a method for selectively removing acyl groups from taxane compounds.

Another object of the present invention is to provide a method for selectively removing acetyl groups from taxane compounds.

Additional objects, advantages, and novel features of this invention shall be set forth in part in the description and examples that follow, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

To achieve the foregoing and other objects and in accordance with the purposes of the present invention, as embodied and broadly described therein the method of this invention comprises contacting a taxane compound with a mixture of solvent and peroxide in the presence of a base.

BRIEF DESCRIPTION OF THE DRAWINGS

The accompanying drawings, which are incorporated in and form a part of the specifications, illustrate the preferred embodiments of the present invention, and together with the descriptions serve to explain the principles of the invention.

In the Drawings.

DETAILED DESCRIPTION OF THE PREFERRED EMBODIMENT

The present invention relates to a highly selective one step process for the deacylation (or deacetylation) of taxane compounds by dissolving the taxant compound in a solvent, such as, tetrahydrofuran (THF) and contacting the resulting solution with a peroxide, preferably hydrogen peroxide followed by the addition of a specific base.

Figure 1:
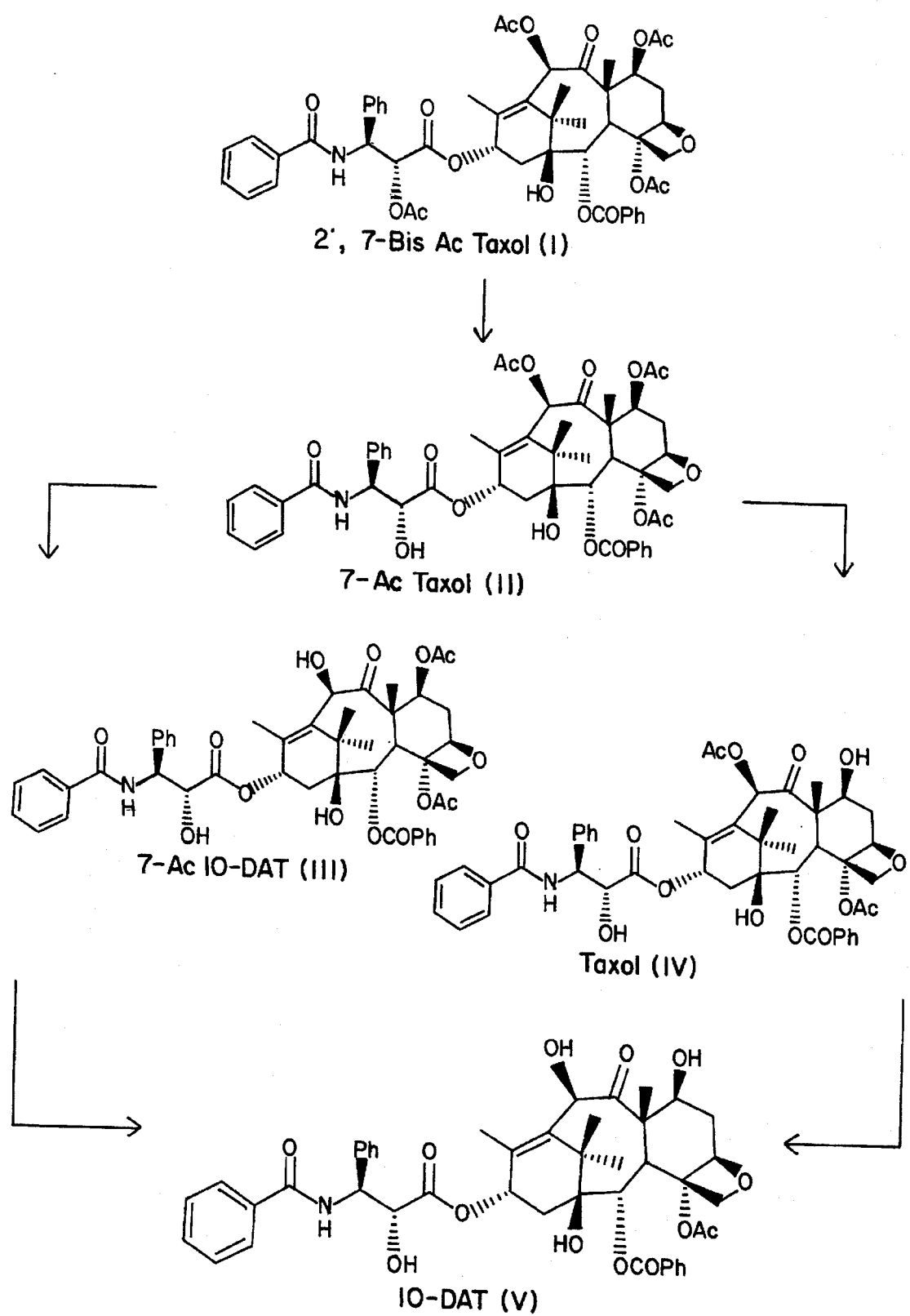
FIG. 1 is a diagrammatic representation of the resulting products formed from 2', 7(bis) acetyl - taxol (2', 7-Bis Ac Taxol) according to the process of the present invention.

The process of the present invention is best illustrated in FIG. 1, while the highly specific selectivity of acyl group removal is demonstrated in the data presented in Table 1, as discussed in further detail below. It is to be understood that acetyl groups are a subset of acyl groups and for purposes of this invention the acyl group will be generally referred to. As shown in FIG. 1, a taxane compound such as 2', 7-Bis Ac Taxol having structure (I) is dissolved in a solvent such as THF, preferably 0.03 ml/mg of taxane compound at a temperature in the range of 0°–50° C. To this solution approximately 0.05 ml/mg of a peroxide such as hydrogen peroxide is added followed by the addition of approximately 10 mg/mg of a specific base. Among the preferred bases are calcium carbonate ($CaCO_3$) and sodium bicarbonate ($NaHCO_3$); however, other bases such as sodium carbonate ($Na_2CO_3$), barium carbonate ($BaCO_3$), and sodium hydroxide (NaOH), etc. may be used. The aforementioned list is exemplary of the bases that may be used and is not meant to limit the scope of the present invention. The acyl group located at the 2' position of (I) is the most reactive group and consequently the first group to be removed from 2', 7-Bis Ac Taxol following the addition of the base resulting in 7-Ac Taxol or structure (II). The reactivity of the groups positioned at the C-10 and C-7 positions are similar; however, removal from the C-10 position is slightly favored over removal from the C-7 position. Consequently, following the formation of 7-Ac Taxol, the 7-Ac 10-DAT, or structure (III) is the major compound formed while taxol or structure (IV) is the minor compound formed. The reaction is allowed to proceed resulting in the removal of the groups located at the C-7 and C-10 positions of (III) and (IV), respectively, resulting in the formation of 10-DAT or structure (V).

Table I below summarizes the rates and selectivities of the deacetylation reaction using various bases. The starting material for each individual reaction was Bis-Ac taxol or 2', 7-Bis Ac taxol (I), while the only variable in each reaction was the specific base used. The reaction mixtures were sampled over time for HPLC analysis resulting in percentages based on chromatographic purifies. A more specific description of the conditions for each specific reaction is described below in the Examples section.

TABLE I

| Starting Material | Base | Time | Bis-Ac Taxol (%) | 7-Ac Taxol (%) | Taxol (%) | 10-DAT (%) |
| --- | --- | --- | --- | --- | --- | --- |
| 2',7-bis AC Taxol | $NaHCO_3$ | 30 min | ND | 96.3 | 0.6 | ND |
| or (Bis-AC Taxol) |  | 24 hr | ND | 42.3 | 2.3 | 47.7 |
|  | $NaHCO_3$, (5 eq) | 30 min | ND | 81.0 | 0.9 | 1.5 |
|  |  | 24 hr | ND | 47.6 | 2.0 | 34.1 |
|  | $Na_2CO_3$ | 15 min | ND | 76.1 | 1.0 | 8.1 |
|  |  | 24 hr | ND | ND | 20.0 | 16.6 |
|  | $CaCO_3$ | 30 min | 3.2 | 92.9 | 0.5 | 0.9 |
|  |  | 24 hr | ND | 78.8 | 1.1 | 13.4 |
|  | $CaCO_3$, (5 eq) | 30 min | 14.1 | 82.3 | ND | ND |
|  |  | 24 h | 0.7 | 88.9 | 0.6 | 4.0 |
|  | $BaCO_3$ | 30 min | 11.0 | 79.8 | 0.3 | ND |
|  |  | 24 hr | ND | 89.0 | 0.6 | 3.6 |
|  | $Ba(OH)_2$ | 30 min | 17.6 | 71.4 | 1.3 | 1.4 |
|  |  | 24 hr | ND | 53.5 | 2.4 | 2.1 |
|  | $CdCO_3$ | 30 min | 73.1 | 26.5 | ND | ND |
|  |  | 24 hr | 44.0 | 54.7 | ND | ND |

TABLE I-continued

| Starting Material | Base | Time | Bis-Ac Taxol (%) | 7-Ac Taxol (%) | Taxol (%) | 10-DAT (%) |
|---|---|---|---|---|---|---|
| | $Cs_2CO_3$ | 30 min | ND | 41.4 | 0.5 | 12.8 |
| | | 90 min | ND | 3.0 | 2.3 | 39.4 |
| | | 24 hr | ND | ND | ND | ND |

ND = none detected

Surprisingly, the reactions summarized in Table I above do not lead to epimerization of the C-7 position resulting in any detectable 7-epi product. The value of this result is that it alleviates the need to protect the C-7 position. The 7-epi product only becomes detectable following prolonged reaction conditions. As summarized below in Tables 1a and 1b, the 7-epi product is produced from taxol and baccatin, respectively, under prolonged periods of time. However, even in prolonged reaction conditions the base $CaCO_3$ may be used to minimize the formation of the 7-epi product.

TABLE 1a

| Starting Material | Solvent | Base | Time | Taxol (% CP) | 10-DAT (% CP) | 7-epi-10-DAT (% CP) |
|---|---|---|---|---|---|---|
| Taxol | $H_2O$ | $NaHCO_3$ | 4 days | 86.3 | 9.1 | 0.6 |
| | THF | $NaHCO_3$ | 4 days | ND | 79.5 | 13.2 |
| | THF | $CaCO_3$ | 4 days | ND | 95.4 | 3.9 |

ND = none detected

TABLE 1b

| Starting Material | Solvent | Base | Time | Baccatin (% CP) | 10-DAB (% CP) | 7-epi-10-DAB (% CP) |
|---|---|---|---|---|---|---|
| Baccatin | $H_2O$ | $NaHCO_3$ | 4 days | 19.1 | 29.7 | 28.1 |
| | THF | $NaHCO_3$ | 6 hrs. | 17.4 | 72.2 | 4.6 |
| | | | 4 days | ND | 50.1 | 42.4 |

ND = none detected

As demonstrated in the Examples that follow, the substrate to be used may be any taxane compound and the resulting products produced are dependent upon the extent to which the deacylation reactions is allowed to occur.

The following non-limited examples provide high yield processes for the specific deacetylation and deacylation of taxol and other taxanes. All scientific and technical terms have the meanings as understood by one with ordinary skill in the art. HPLC was performed on a Hitachi chromatographic spectrometer (L-6200A Intelligent Pump, D-6000 Interface, L-4000 UV Detector and AS-4000 Intelligent Auto Sampler). Combination of $CH_3CN$ and $H_2O$ in different concentrations are used as HPLC solvent system. All solvents were distilled before use. Commercially available chemicals were used without any further purification. Various methods of purifying the products of the present invention are known and understood by those skilled in the art and the purification methods presented in the Examples is solely by way of example and is not intended to limit the invention.

EXAMPLE I

Large Scale Reaction of Taxol with $NaHCO_3$: 500 mg (0.57 mmol) of taxol in 10 ml of THF were introduced into a 25 ml round bottomed flask equipped with a magnetic stir bar. 10 ml of 30% $H_2O_2$ was added followed by 960.0 mg of $NaHCO_3$ and the mixture was then stirred at room temperature overnight. The mixture was then extracted with methylene chloride/water (50:50 by volume). The organic phase was collected and dried over anhydrous magnesium sulfate. The solvent was then evaporated under reduced pressure to obtain a crude product, that was subsequently purified. 457.2 mg of pure 10-deacetyltaxol were recovered resulting in a 96% yield. NMR data and mass spec. match known samples.

EXAMPLE II

Small Scale Reaction of Taxol with $NaHCO_3$: 10 mg (0.01 mmol) of taxol in 1 ml of THF were introduced into a 4 ml vial equipped with a magnetic stir bar. 0.5 ml of 30% $H_2O_2$ was added followed by 100 mg of $NaHCO_3$ and the mixture was then stirred at room temperature overnight. The mixture was then extracted with methylene chloride/water (50:50 by volume). The organic phase was collected and dried over anhydrous magnesium sulfate. The solvent was then evaporated under reduced pressure to obtain a crude product, that was subsequently purified. The results of which are summarized below in Table 2.

EXAMPLES III-X

The following Examples III-X were performed under the same conditions as Example II above except the base was changed as indicated.

Figure 2:
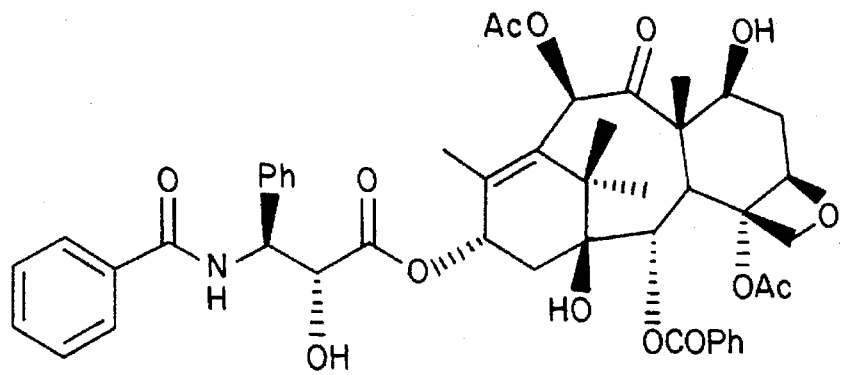
FIG. 2 is a diagrammatic representation of the products formed when taxol is selectively deacetylated according to the process of the present invention.
Figure 2:
Figure 2:
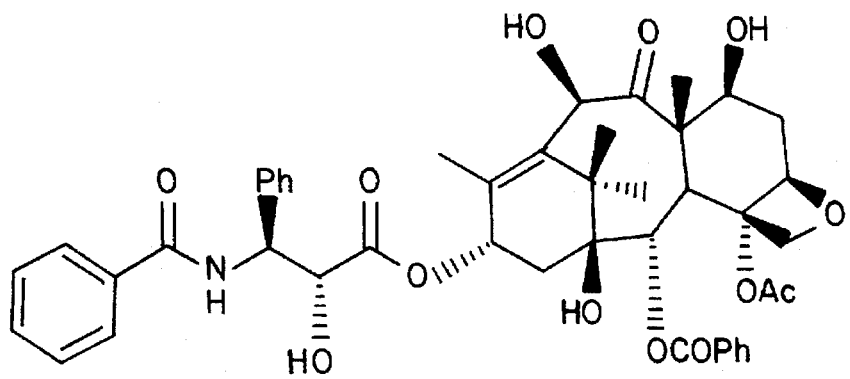

Reaction of Taxol with LiOH
Reaction of Taxol with NaOH
Reaction of Taxol with $Na_2CO_3$
Reaction of Taxol with $K_2CO_3$
Reaction of Taxol with KCl
Reaction of Taxol with $CaCO_3$ Reaction of Taxol with $Ca(OH)_2$ Reaction of Taxol with no base Product The process of the present invention when performed on taxol as the starting compound is illustrated in FIG. 2.

The results of these reactions using various bases is summarized in Table 2 below.

TABLE 2

| Substrate/Products | Base | Time (Hrs) | 10-DAT (% CP) | Taxol (% CP) | 10-DAB (% CP) |
|---|---|---|---|---|---|
| taxol/ | LiOH | 1.5 | 21.7 | 11.1 | 29.7 |
| 10-DAT, | NaOH | 1.5 | 61.8 | 13.3 | 12.2 |
| 10-DAB | | 24 | 0.95 | | 20.0 |
| | $Na_2CO_3$ | 1.5 | 87.8 | 4.7 | 5.2 |
| | | 24 | 10.8 | | 55.7 |
| | $NaHCO_3$ | 1.5 | 26.1 | 72.8 | |
| | | 24 | 91.6 | 4.6 | |
| | $K_2CO_3$ | 1.5 | 82 | 8.4 | 7.3 |
| | KCl | 1.5 | 7.7 | 91.4 | |
| | $CaCO_3$ | 1.5 | 49.9 | 49.7 | 1.0 |
| | | 16 | 97.4 | 1.6 | |
| | $Ca(OH)_2$ | 1.5 | 62.4 | 15.6 | 13.9 |
| | | 16 | | | 34.7 |
| | None | 14 | 1.5 | 96.9 | ND |
| | | 48 | 3.1 | 95.6 | ND |

EXAMPLE XI

Figure 3:
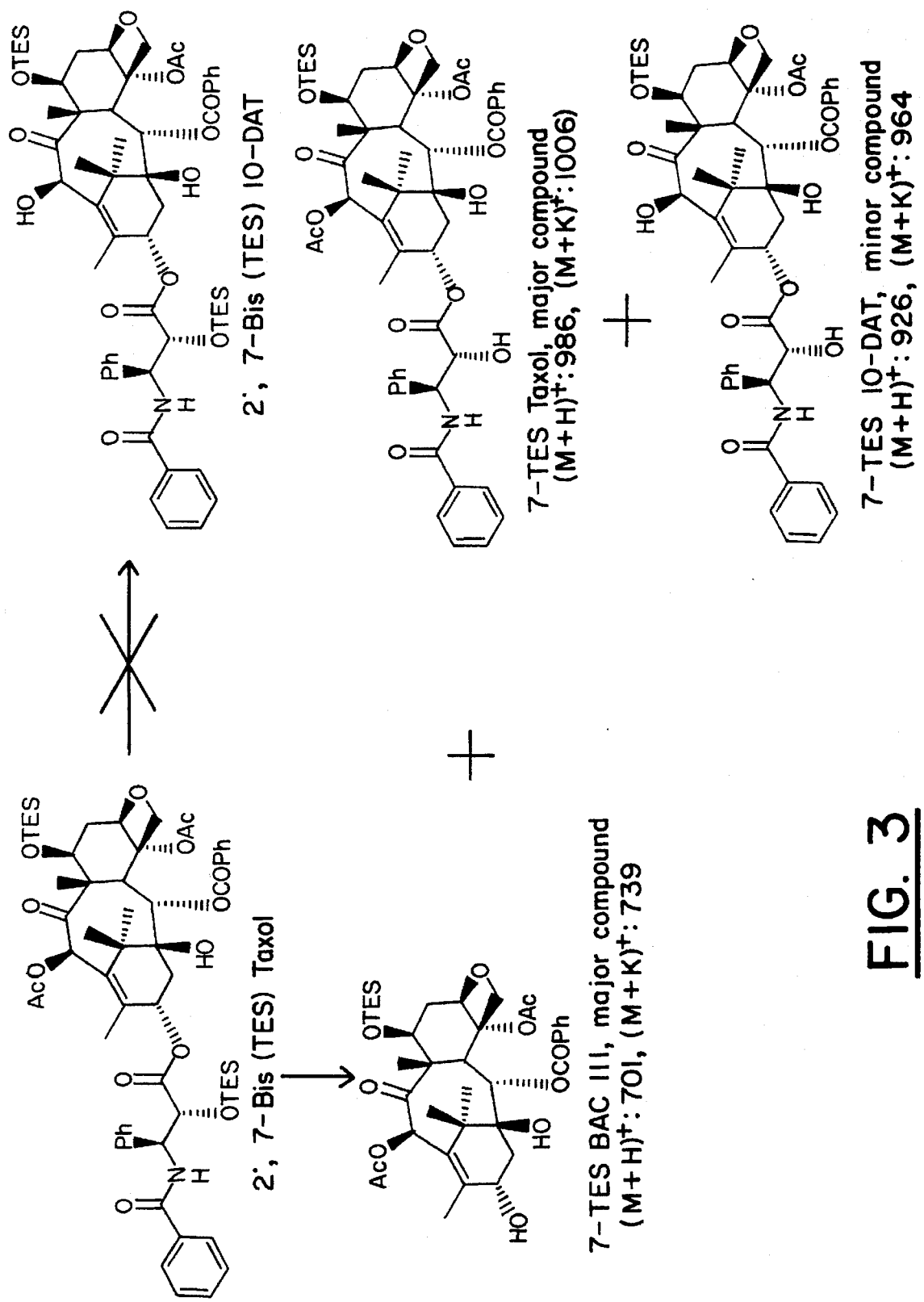
FIG. 3 is a diagrammatic representation of the products formed when 2', 7-Bis (TES) Taxol is selectively deacetylated according to the process of the present invention.

Reaction of 2', 7 Bis-(TES) Taxol with $Na_2CO_3$: 10 mg (0.01 mmol) of 2', 7 Bis-(TES) Taxol wherein TES is shorthand for triethysilyl, in 0.5 ml of THF were introduced into a 4 ml vial equipped with a magnetic stir bar. 0.5 ml of 30% $H_2O_2$ was added followed by mg of $Na_2CO_3$ and the mixture was then stirred at room temperature overnight. The mixture was then extracted with methylene chloride/water (50:50 by volume). The organic phase was collected and dried over anhydrous magnesium sulfate. The solvent was then evaporated under reduced pressure to obtain a crude product, that was subsequently purified. HPLC and MS was used to monitor the reactions. Three new products illustrated in FIG. 3 were formed. The major product being 7-(TES) Taxol, while the minor products are 7-(TES) BAC III and 7-(TES) 10-DAT.

EXAMPLE XII

Reaction of 2', 7 Bis-(TES) Taxol with $NaHCO_3$: Performed in the same manner as Example XI above. No reaction was detected.

EXAMPLE XIII

Reaction of 7-epi-taxol with $NaHCO_3$: 10 mg (0.01 mmol) of 7-epi-taxol with $NaHCO_3$ in 0.3 ml of THF were introduced into a 4 ml vial equipped with a magnetic stir bar. 0.5 ml of 30% $H_2O_2$ was added followed by 100 mg $NaHCO_3$ and the mixture was then stirred at room temperature overnight. The mixture was then extracted with methylene chloride/water (50:50 by volume). The organic phase was collected and dried over anhydrous magnesium sulfate. The solvent was then evaporated under reduced pressure to obtain a crude product 7-epi-10-deacetyl taxol, that was subsequently purified. Following a 48 hour reaction 25.4% chromo. purity of starting material and 48.3% chrom. purity of 7-epi-10-deacetyl taxol resulted.

EXAMPLE XIV

Reaction or Baccatin III with $NaHCO_3$: 50 mg (0.085 mmol) of Baccatin III in 1.5 ml of THF were introduced into a 25 ml round bottomed flask equipped with a magnetic stir bar. 2.5 ml of 30% $H_2O_2$ was added followed by 500 mg of $NaHCO_3$ and the mixture was then stirred at room temperature overnight. The major product after 15 hours was 10-deacetyl baccatin III. Some 7-epi 10-deacetyl baccatin was also present (9.1% crude product).

EXAMPLE XV

All of the above Examples were carried out in the organic solvent tetrahydrofuran using hydrogen peroxide. Several experiments, the results of which are summarized below in Table 3, were carded out in order to determine the effect of different peroxides on the deacylation of taxol to 10-deacytyltaxol. Approximately 10 mg of taxol was dissolved in 0.3 ml of THF. The peroxide was then added to the reaction mixture followed by the addition of 100 mg $NaHCO_3$ which was subsequently stirred at room temperature for the time indicated in Table 3.

TABLE 3

| Solvent | Peroxide | Time (hr) | 10-DAT (% CP) | Taxol (% CP) |
|---|---|---|---|---|
| THF | 70% aq t-BuOOH | 24 | 1.3 | 97.3 |
| | (0.5 ml; 310 eq) | 48 | 2.9 | 95.8 |
| THF | 80% MMPP (300 mg; | 24 | 0.0 | 100.0 |
| | 40 eq) | 48 | 0.9 | 98.3 |
| THF | 50-60% MCPBA | 24 | 0.0 | 99.5 |
| | (300 mg; 80 eq) | 48 | 0.0 | 98.6 |

No 10-DAT was seen in the first 48 hours of the reactions where MCPBA (3-chloroperoxybenzoic acid) replaced hydrogen peroxide; however, there was a small amount of 10-DAT formed in the t-BuOOH (tert-butyl hydrogen) peroxide and MMPP (monoperoxyphethalic acid magnesium salt hexahydrate) experiments suggesting other peroxides may be useful for this conversion. The data also shows that these reactions can be carded out in many solvents; however, better conversion is seen in the more polar solvents.

EXAMPLE XVI

Several experiments, the results of which are summarized below in Tables 4 and 5, were carded out in order to determine the effect of various solvents on the deacetylation of taxol and baccatin, respectively. Approximately 10 mg of starting material (listed below) was dissolved in 0.3 ml of the solvent indicated in Tables 4 and 5. To the solution was added 0.5 ml $H_2O_2$ and 100 mg of $NaHCO_3$ base for the time indicated in Tables 4 and 5.

TABLE 4

| Starting Material | Solvent | Time | Taxol (% CP) | 10-DAT (% CP) | 10-DAB (% CP) |
|---|---|---|---|---|---|
| Taxol | MeOH | 24 hrs. | 78.1 | 21.0 | |
| | | 48 hrs. | 54.6 | 42.5 | |
| | $CH_2Cl_2$ | 24 hrs. | 97.9 | 1.8 | |
| | | 48 hrs. | 95.2 | 3.3 | |
| | Acetone | 24 hrs. | 29.9 | 69.4 | |
| | | 48 hrs. | 16.5 | 77.7 | |
| | $H_2O$ | 4 days | 83.6 | 9.1 | |
| | $H_2O$ (1.0 ml) | 24 hrs. | 20.4 | 71.4 | 5.1 |
| | Acetone (1.0) | 41 hrs. | 23.1 | 56.5 | 9.2 |
| | Acetone (1.0) | 24 hrs. | 75.8 | 23.9 | ND |
| | $H_2O$ (1.0 ml) | 41 hrs. | 47.8 | 19.6 | 7.9 |
| | $H_2O$ (1.0 ml) | 24 hrs. | 52.1 | 43.3 | 2.7 |
| | MeOH (1.0 ml) | 41 hrs. | 17.9 | 51.8 | 12.1 |

ND = none detected

When taxol is used as the starting material the reaction using water as the solvent does proceed to the 10-DAT product; however, the rate is very slow.

TABLE 5

| Starting Material | Solvent | Time | Baccatin III | 10-DAB |
|---|---|---|---|---|
| Baccatin III | THF | 2.5 hrs. | 45.8 | 47.2 |
| | | 6.0 hrs. | 17.4 | 72.2 |
| | H₂O | 6.0 hrs. | 66.7 | 15.9 |
| | | 4 days | 19.1 | 29.7 |

When Baccatin III was used as the starting material the reaction using water as the solvent also proceeds to the 10-DAB product; however, with a prolonged reaction time the yield is low and the 7-epi-10-DAB was formed in considerable amounts.

The embodiments of the invention in which an exclusive property or privilege is claimed are defined as follows:

1. A process for selectively removing acyl group(s) located at the C-2', C-7, and/or C-10 position(s) of a taxane compound comprising the steps of:

dissolving the taxane compound in a quantity of solvent whereby a taxane solution is produced;

adding a peroxide to said taxane solution;

adding a base to said taxane solution containing said peroxide whereby a reaction mixture is produced; and stirring said reaction mixture.

2. The process of claim 1, wherein said taxane compound is taxol.

3. The process of claim 1, wherein said taxane compound is 2', 7 Bis Acyl Taxol.

4. The process of claim 1, wherein said taxane compound is 7-epi-taxol.

5. The process of claim 1, wherein said taxane compound is Baccatin III.

6. The process of claim 1, wherein said taxane compound is 2', 7 Bis (TES) Taxol.

7. The process of claim 1, wherein said taxane compound is 2', 7-Bis Acetyl Taxol.

8. The process of claim 1, wherein said solvent is tetrahydrofuran.

9. The process of claim 1, wherein said peroxide is a hydrogen peroxide.

10. The process of claim 1, wherein said base is NaHCO₃.

11. The process of claim 1, wherein said stirring step proceeds for a period of time sufficient to remove said acyl group located at the C-2' position of said taxane compound.

12. The process of claim 1, wherein said acyl group having the structure

wherein R, is defined as an alkane.

13. A process for selectively removing acyl group(s) located at the C-2', C-7 and/or C-10 position(s) of a taxane compound comprising the steps of:

dissolving the taxane compound in tetrahydrofuran whereby a taxane solution is produced;

adding hydrogen peroxide to said taxane solution;

adding a base to said taxane solution containing hydrogen peroxide whereby a reaction mixture is produced; and stirring said reaction mixture.

14. The process of claim 13, wherein said base is sodium bicarbonate.

15. The process of claim 13, wherein said base is calcium carbonate.

16. The process of claim 1, wherein said stirring step proceeds for a period of time sufficient to remove said acyl group located at the C-7 position of said taxane compound.

17. The process of claim 1, wherein said stirring step proceeds for a period of time sufficient to remove said acyl group located at the C-10 position of said taxane compound.

18. The process of claim 1, wherein said base is LiOH.

19. The process of claim 1, wherein said base is NaOH.

20. The process of claim 1, wherein said base is Na₂CO₃.

21. The process of claim 1, wherein said base is K₂CO₃.

22. The process of claim 1, wherein said base is CaCO₃.

23. The process of claim 1, wherein said base is Ca(OH)₂.

24. The process of claim 1, wherein said base is BaCO₃.

25. The process of claim 1, wherein said base is Ba(OH₂).

26. The process of claim 1, wherein said base is CdCO₃.

27. The process of claim 1, wherein said base is Cs₂CO₃.

28. A process for the selective deacylation of a taxane compound having acyl group(s) located at the C-2', C-7 and/or C-10 position(s) comprising the steps of:

dissolving the taxane compound in a solvent whereby a taxane solution is produced;

adding approximately 0.05 ml of a peroxide per mg of the taxane in said taxane solution to said taxane solution;

adding NaHCO₃ to said taxane solution containing said peroxide whereby a reaction mixture is produced; and stirring said reaction mixture for a period of time sufficient to remove the desired acyl group(s) positioned at the C-2', C-7 and/or C-10 position(s) of said taxane compound.

* * * * *